(12) United States Patent
Kalbfeld et al.

(10) Patent No.: US 8,663,520 B2
(45) Date of Patent: Mar. 4, 2014

(54) INTERDENTAL CLEANERS AND METHODS FOR MAKING SAME

(75) Inventors: Russell G. Kalbfeld, Naperville, IL (US); Leoncio Angel Gonzalez, Winfield, IL (US)

(73) Assignee: Sunstar Americas, Inc., Chicago, IL (US)

( * ) Notice: Subject to any disclaimer, the term of this patent is extended or adjusted under 35 U.S.C. 154(b) by 709 days.

(21) Appl. No.: 12/510,852

(22) Filed: Jul. 28, 2009

(65) Prior Publication Data

US 2010/0024839 A1 Feb. 4, 2010

Related U.S. Application Data

(60) Provisional application No. 61/084,573, filed on Jul. 29, 2008.

(51) Int. Cl.
*B29C 37/00* (2006.01)

(52) U.S. Cl.
USPC .............................. 264/138; 364/155; 364/250

(58) Field of Classification Search
USPC ........................................ 264/138, 155, 250
See application file for complete search history.

(56) References Cited

U.S. PATENT DOCUMENTS

| | | |
|---|---|---|
| 1,527,845 A | 2/1925 | Daniel |
| 1,581,501 A | 4/1926 | Wright |
| 1,746,591 A | 2/1930 | Heymann et al. |
| 3,078,856 A | 2/1963 | Bender et al. |
| 3,590,814 A | 7/1971 | Bennett et al. |
| 3,775,848 A | 12/1973 | Barnett |
| 3,779,256 A | 12/1973 | Maloney et al. |
| 4,319,377 A | 3/1982 | Tarrson et al. |
| 4,326,547 A | 4/1982 | Verplank |
| 4,832,063 A | 5/1989 | Smole |
| 4,974,615 A | 12/1990 | Doundoulakis |
| 5,246,021 A | 9/1993 | Katz |
| 5,392,794 A | 2/1995 | Striebel |
| 5,775,346 A | 7/1998 | Szyszkowski |

(Continued)

FOREIGN PATENT DOCUMENTS

| | | |
|---|---|---|
| CN | 1329475 | 1/2002 |
| EP | 0707836 | 4/1996 |

(Continued)

OTHER PUBLICATIONS

International Search Report and Written Opinion, International Application No. PCT/US2009/051979, dated Sep. 3, 2009.
EP 09803491.1 Extended European Search Report and Opinion dated Mar. 7, 2013 (9 pages).

(Continued)

*Primary Examiner* — James Sanders
(74) *Attorney, Agent, or Firm* — Michael Best & Friedrich LLP

(57) ABSTRACT

A method of making interdental cleaners includes forming a slug by extruding material in a direction of extrusion to form a first slug portion having a generally rectangular first cross-section and a second slug portion having a tapering second cross-section that extends away from the rectangular first cross-section. The method also includes stamping the slug substantially perpendicular to the direction of extrusion to form a plurality of cleaner blanks. The stamping forms the first slug portions into handle portions of the cleaner blanks, and the second slug portions into shaft portions of the cleaner blanks. The shaft portions include two pairs of converging surfaces that taper toward each other to define a point. The method also includes attaching cleaning members to the ends of the shaft portions.

20 Claims, 12 Drawing Sheets

(56) References Cited

U.S. PATENT DOCUMENTS

| | | |
|---|---|---|
| 5,806,540 A | 9/1998 | Lee |
| 5,987,688 A | 11/1999 | Roberts et al. |
| 6,158,444 A | 12/2000 | Weihrauch |
| 6,220,258 B1 | 4/2001 | Briggs et al. |
| 6,669,475 B2 | 12/2003 | Kandelman et al. |
| 2001/0035193 A1 | 11/2001 | Narayanan |
| 2004/0164454 A1 | 8/2004 | Gartstein et al. |

FOREIGN PATENT DOCUMENTS

| | | |
|---|---|---|
| EP | 1972305 | 9/2008 |
| JP | 11192245 | 7/1999 |
| JP | 4581716 | 11/2010 |
| WO | 02/15814 | 2/2002 |
| WO | 2004076339 | 9/2004 |

OTHER PUBLICATIONS

First Office Action from the State Intellectual Property Office of China for Application No. 2009801328701 dated Nov. 16, 2012 (19 pages).

Office Action from Canadian Intellectual Property Office for Application No. 2,731,639 dated Mar. 28, 2013 (2 pages).

Office Action from Colombian Patent Office for Application No. 11-009-800 dated Apr. 22, 2013 with English translation of relevant sections (15 pages).

Office Action from Mexican Institute of Industrial Property for Application No. MX/a/2011/001160 dated Jun. 12, 2013 with English translation of relevant sections (5 pages).

Office Action from Colombian Patent Office for Application No. 11-009-800 dated Oct. 13, 2013 with English translation of relevant sections (5 pages).

Second Office Action from Mexican Institute of Industrial Property for Application No. MX/a/2011/001160 dated Sep. 13, 2013 with English translation of relevant sections (7 pages).

INTERDENTAL CLEANERS AND METHODS FOR MAKING SAME

CROSS-REFERENCE TO RELATED APPLICATION

This application claims the benefit of and priority to U.S. Provisional Patent Application No. 61/084,573 filed Jul. 29, 2008, the entire contents of which are hereby incorporated by reference.

BACKGROUND

The present invention relates generally to interdental cleaners and methods for making interdental cleaners.

Interdental cleaning is a principal element of oral hygiene. The spaces between teeth allow plaque and other debris to collect which can harm the gums and teeth. Dental floss is often used to eliminate such debris from the interdental spaces. Dental floss is often cumbersome to use because it requires two hands for proper manipulation of the floss into and out of the interdental spaces. Dental floss is also problematic for patients with certain types of dental appliances (e.g., braces or dental bridges) because it may be difficult or impossible to manipulate the floss into or around the appliance. The interdental cleaner alleviates these shortfalls because it may be manipulated into interdental space otherwise unreachable by traditional flossing methods using a single hand. Because interdental cleaners are generally single-use items, it is beneficial to employ fast, efficient, and cost effective processes for their manufacture.

SUMMARY

In some aspects, the invention may provide a method for making interdental cleaners that includes forming a slug by extruding material in a direction of extrusion, which includes forming a first slug portion having a first cross-section and a second slug portion having a second cross section that is different from the first cross-section. The extruded slug is also formed to define a midplane that is substantially parallel to the direction of extrusion. The method also includes stamping the slug in a direction of stamping that is substantially normal to the midplane to produce a plurality of cleaner blanks. Each cleaner blank is formed to include a handle portion and a shaft portion, and is formed to be oriented along the midplane with the shaft portions extending substantially perpendicular to the direction of extrusion. The method also includes attaching a cleaning member to each shaft portion.

In other aspects, the invention may provide a method of making interdental cleaners that includes forming a slug by extruding material in a direction of extrusion, which includes forming a first slug portion having a first cross-section and a second slug portion having a second-cross section that is different from the first cross-section. The slug is formed to define a midplane and such that the second slug portion defines a first pair of converging surfaces that converge toward the midplane. The method also includes stamping the slug in a direction that is substantially normal to the midplane to form a plurality of cleaner blanks. Each cleaner blank is formed to include a handle portion formed from the first slug portion and a shaft portion formed from the second slug portion. Stamping the slug also includes forming each shaft portion to include a second pair of converging surfaces. The method also includes attaching cleaning members to a portion of the shaft portion.

In still other aspects, the invention may provide a method of making interdental cleaners that includes forming a slug by extruding material in a direction of extrusion to form a first slug portion having a first cross-section and a second slug portion adjacent the first slug portion and having a second cross-section that is different from the first cross-section. The method also includes stamping the slug substantially perpendicular to the direction of extrusion to form a plurality of cleaner blanks. The stamping includes stamping the first slug portion to form handle portions of the cleaner blanks, and stamping the second slug portion to form shaft portions of the cleaner blanks. The method also includes attaching cleaning members to the shaft portions.

DETAILED DESCRIPTION

Figure 1:
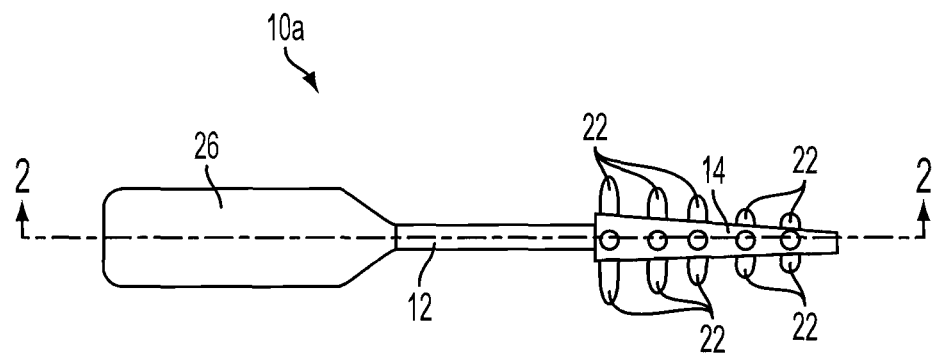
FIG. 1 is a front view of a first embodiment of an interdental cleaner that includes an exposed support structure.

It is to be understood that the invention is not limited in its application to the details of construction and the arrangements of the components set forth in the following description or embodiments, or illustrated in the drawings. The invention is capable of other embodiments and of being practiced or being carried out in various ways. Also, it is to be understood that the phraseology and terminology used herein is for the purpose of description and should not be regarded as limiting.

Figure 2:
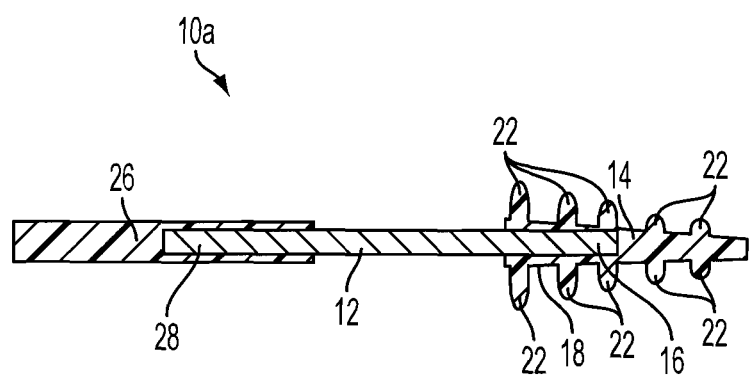
FIG. 2 is a front section view of the interdental cleaner of FIG. 1.
Figure 3:
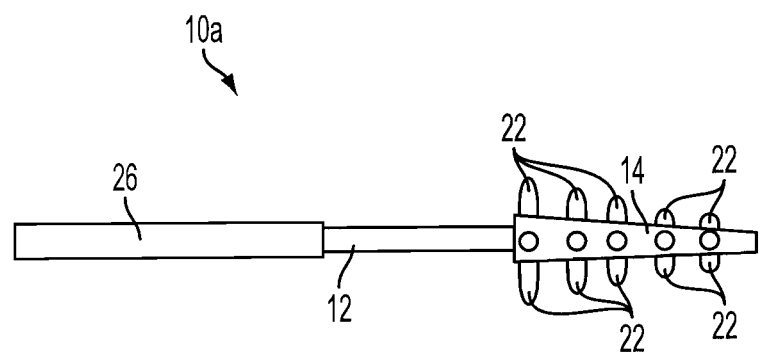
FIG. 3 is a side view of the interdental cleaner of FIG. 1.

FIGS. 1-3 illustrate a first embodiment of an interdental cleaner 10a. The interdental cleaner 10a includes an elongated, substantially rigid central rod 12, which in the illustrated construction is or includes a metallic (e.g., steel) wire. The rod 12 may be formed of, among other things, one or more braided metallic wires, solid metallic wires and/or extruded polymers or plastics, such as monofilament nylon. The interdental cleaner 10a includes cleaning member 14 positioned at a first end 16 of the central rod 12. The cleaning member 14 is generally formed from a plastic material that is suitable for use in the mouth and that is sufficiently hard to provide cleaning of interdental spaces, but sufficiently soft so as not to damage the gums of a user. For example, in some constructions, the cleaning member 14 is formed of a thermoplastic elastomer, although other materials may also be used. The cleaning member 14 is generally formed of a material that is softer than the rod 12.

The cleaning member 14 is formed into a shape suitable for cleaning interdental spaces. Such shapes may include, but are not limited to, conical, cylindrical, pyramidal, rectangular or polygonal in nature. In the illustrated construction, the cleaning member 14 is substantially conical in shape and includes a central, generally cylindrical body portion 18 that receives and thereby overlies the first end 16 of the central rod 12. The cleaning member 14 also includes a plurality of bristles 22 that extend radially outwardly from the body portion 18. The bristles 22 vary in length from a shortest length adjacent a distal end of the cleaning member 14, to a longest length adjacent a proximal end of the cleaning member 14, thereby providing the overall substantially conical shape. The substantially conical shape allows the cleaning member 14 to effectively clean interdental spaces of varying sizes dependent upon the extent to which a user inserts the cleaning member 14 into the interdental space.

In the illustrated construction, the cleaning member 14 is coupled to the central rod 12 by over molding and/or adhesion. For an overmolding operation, the first end 16 of the central rod 12 is positioned in a mold cavity that defines the desired shape (e.g., conical) of the cleaning member 14. The cleaning member material (e.g. thermoplastic elastomer) is then injected into the mold cavity and allowed to cool around the first end 16. An adhesive may also be applied to the first end 16 before the molding process to provide additional coupling between the cleaning member 14 and the first end 16. Alternatively, the cleaning member 14 may be molded individually and the first end 16 of the central rod 12 may subsequently be inserted into the body portion 18. Such insertion may be manual or automated, and may also involve or include the application of a suitable adhesive to one or both of the cleaning member 14 and the central rod 12 to provide coupling adhesion therebetween.

The interdental cleaner 10a also includes a handle 26 coupled to a second end 28 of the central rod 12. The handle 26 is generally formed from a plastic (e.g., polypropylene, including glass-filled polypropylene, and/or nylon) having a hardness that is equal to or greater than the plastic used to form the cleaning member 14. In the illustrated construction, the handle 26 is substantially flat and elongated to provide suitable surfaces for grasping by a user. The handle 26 may also be formed into any other suitable shape (e.g., cylindrical) provided that the handle 26 is appropriately sized so as to avoid interfering with a users access to the interdental spaces while also providing for effective gripping and manipulation of the device.

Like the cleaning member 14, the handle 26 is generally coupled to the central rod 12 by overmolding and/or adhesion. For the overmolding operation, the second end 28 of the central rod 12 is inserted into a mold cavity that defines the shape of the handle 26 (e.g., flat and elongated). The mold cavity is then injected with the desired plastic for the handle 26 and allowed to cool. Adhesives may also be applied to provide extra coupling between the end 30 and the handle 26. Alternatively, the handle 26 may be molded individually, and the central rod 12 may be inserted into the handle 26 after the molding process. Insertion of the central rod 12 may be manual and/or automated. As illustrated in FIGS. 1-3, the central rod 12 is exposed between the handle 26 and cleaning member 14, thereby creating a central portion of the interdental cleaner that is of reduced cross section to facilitate interdental cleaning.

Figure 4:
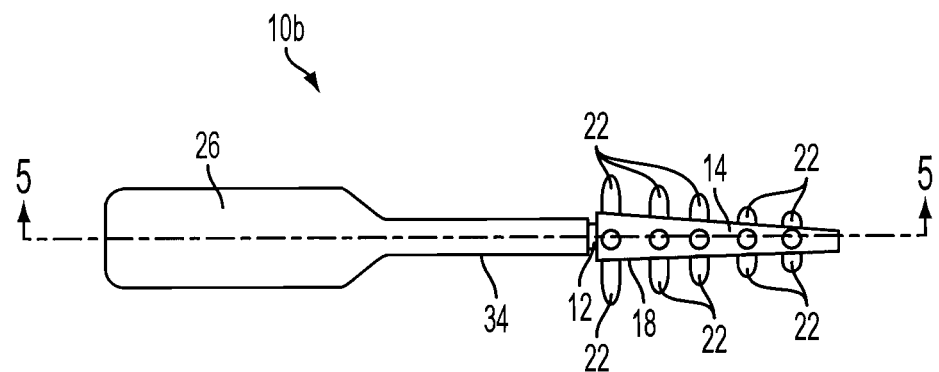
FIG. 4 is a front view of a second embodiment of an interdental cleaner that includes a sheathed support structure.
Figure 5:
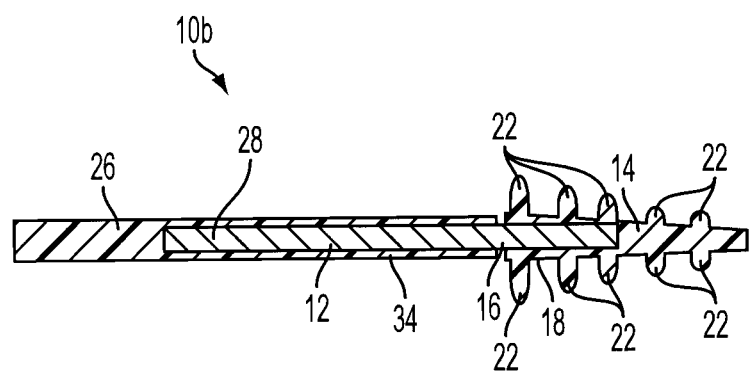
FIG. 5 is a front section view of the interdental cleaner of FIG. 4.
Figure 6:
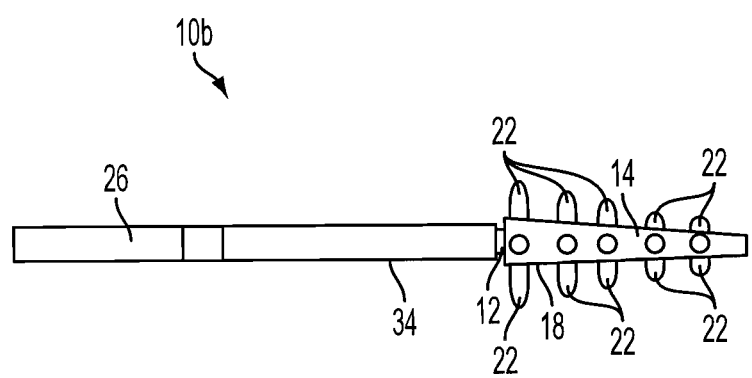
FIG. 6 is a side view of the interdental cleaner of FIG. 4.

FIGS. 4-6 illustrate a second embodiment of an interdental cleaner 10b, in which the handle 26 includes a sheath portion 34 which extends along at least a portion of the central rod 12 toward the cleaning member 14. The sheath 34 covers and in some instances provides additional structural support to the central rod 12. In the illustrated construction, the sheath 34 extends to a location that is near but not directly adjacent to the cleaning member 18. In other constructions the sheath 34 may extend from the handle 26 to the cleaning member 18 to completely cover the central rod 12. The sheath 34 is generally integrally formed with the handle 26, and, like the handle 26, may be coupled to the central rod 12 by overmolding and/or adhesion, as discussed above. In other constructions, the sheath 34 and the handle 26 may be formed separately and subsequently coupled to one another and to the central rod 12. It should be appreciated that substantially any sequence of assembly may be utilized during the manufacture of the handle 26, sheath 34, and the central rod 12.

Figure 7:
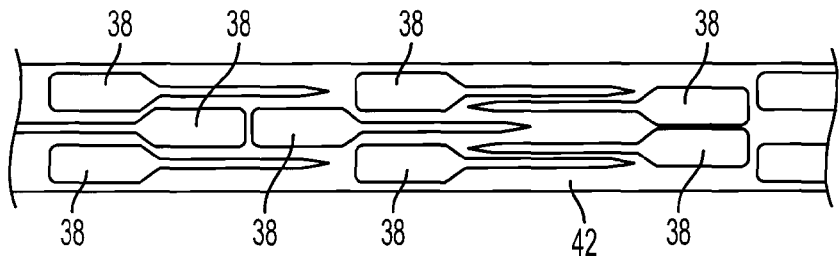
FIG. 7 is a plan view of a first embodiment of extruded material from which interdental cleaner blanks are stamped.
Figure 8:
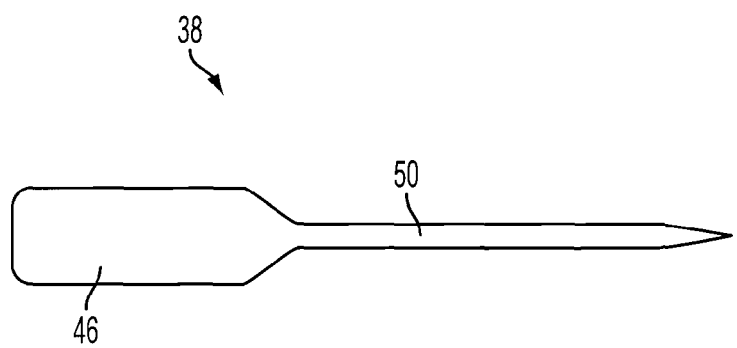
FIG. 8 is a front view of an interdental cleaner blank stamped from the extruded material of FIG. 7.
Figure 9:
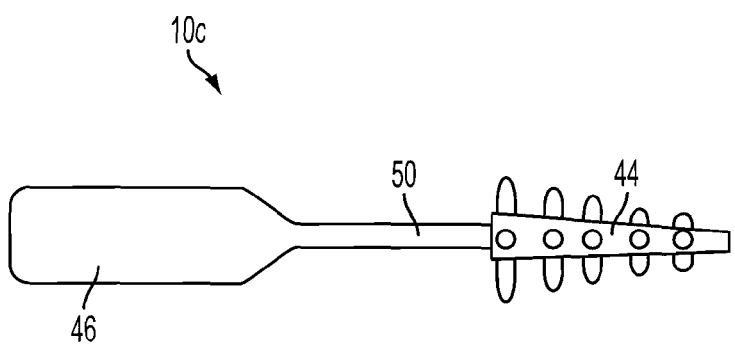
FIG. 9 is a front view of a third embodiment of an interdental cleaner that is formed from the interdental cleaner blank of FIG. 8.

FIGS. 7-9 illustrate a first embodiment of an extrusion (FIG. 7) that is formed into a third embodiment of an interdental cleaner 10c (FIG. 9). The interdental cleaner 10c is formed by stamping cleaner blanks 38 from an extruded slug 42 of an extrudable material that may include, for example, polypropylene (including glass-filled polypropylene) and/or nylon. The extruded slug 42 includes a substantially uniform thickness. After stamping, the cleaner blanks 38 are subsequently overmolded with or otherwise coupled to a cleaning member 44. As shown in FIG. 7, the cleaner blanks 38 are preferably stamped out of the slug 42 in a pattern devised to minimize waste material. Preferably, waste material that remains after stamping of the cleaner blanks 38 is recycled for subsequent extrusion and stamping into additional cleaner blanks 38.

As shown in FIGS. 8 and 9, each cleaner blank 38 includes a handle portion 46 and a shaft portion 50. The handle portion 46 and shaft portion 50 substantially correspond in shape and size to the handle 26 and central rod 12 if the interdental cleaners 10a and 10b discussed above with respect to FIGS. 1-6. After the cleaner blanks 38 are stamped from the extruded strip 42, finishing methods such as tumbling, polishing, or deburring may be employed to remove flash and/or sharp edges from the cleaner blanks 38. Once the cleaner blanks 38 are stamped and, if necessary, finished, cleaning members 44 are formed on or coupled to the distal ends of the shaft portions 50 using cleaning member materials and overmolding or adhesion operations similar to those described above with respect to the cleaning members 10a, 10b.

Figure 10:
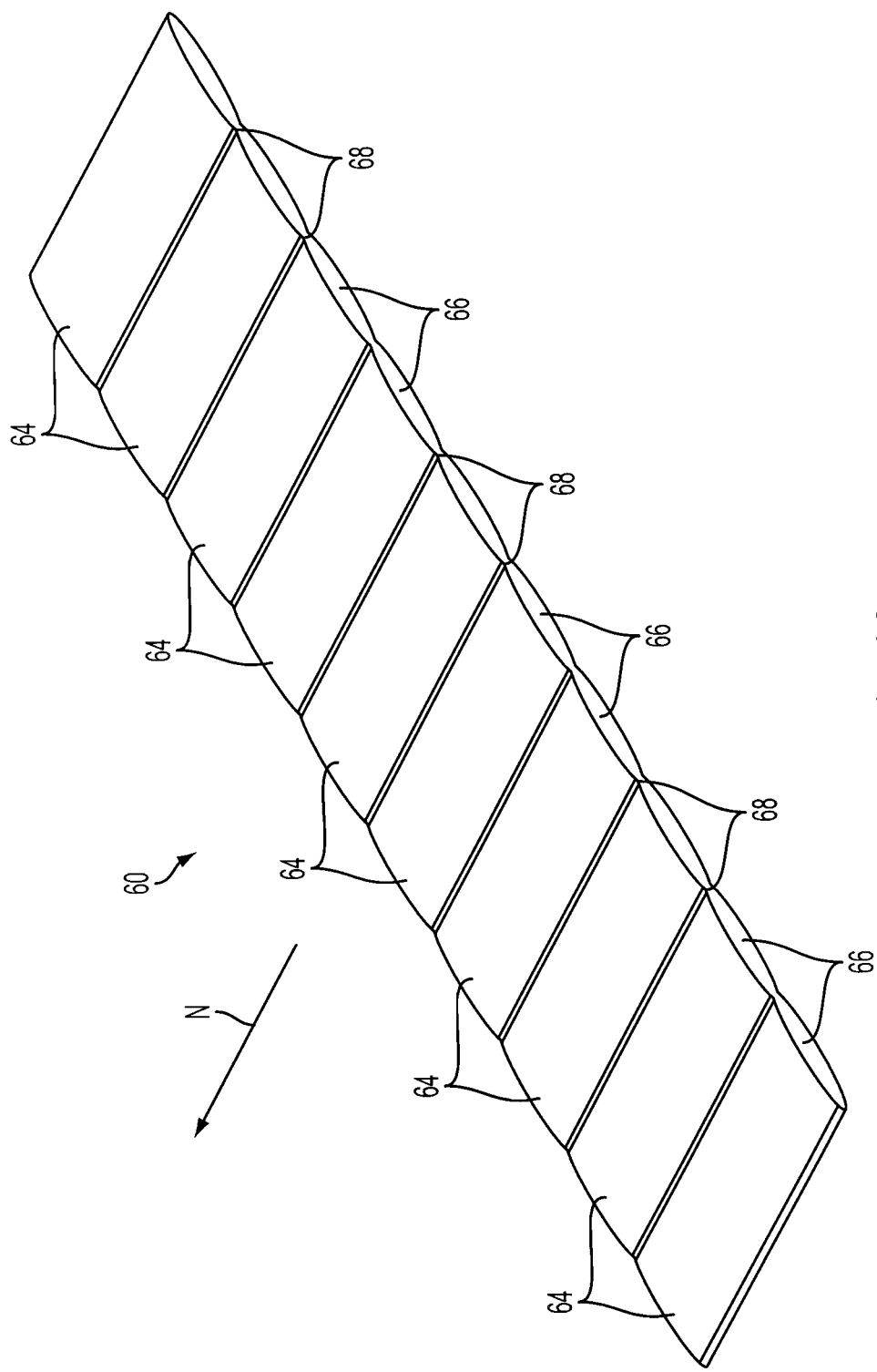
FIG. 10 is an isometric view of a second embodiment of extruded material from which interdental cleaner blanks are stamped.
Figure 11:
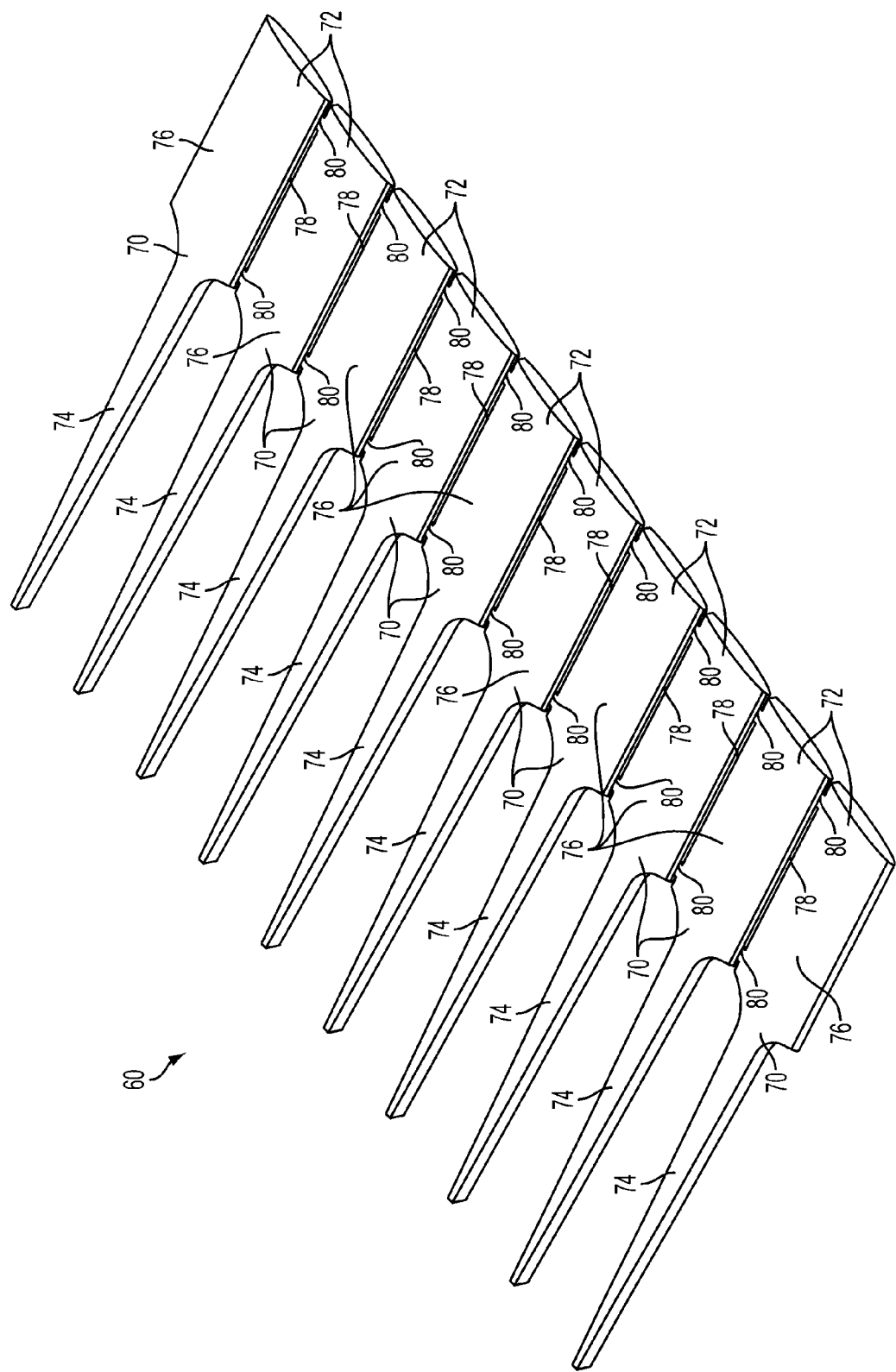
FIG. 11 is an isometric view of interdental cleaner blanks stamped from the extruded material of FIG. 10.
Figure 12:
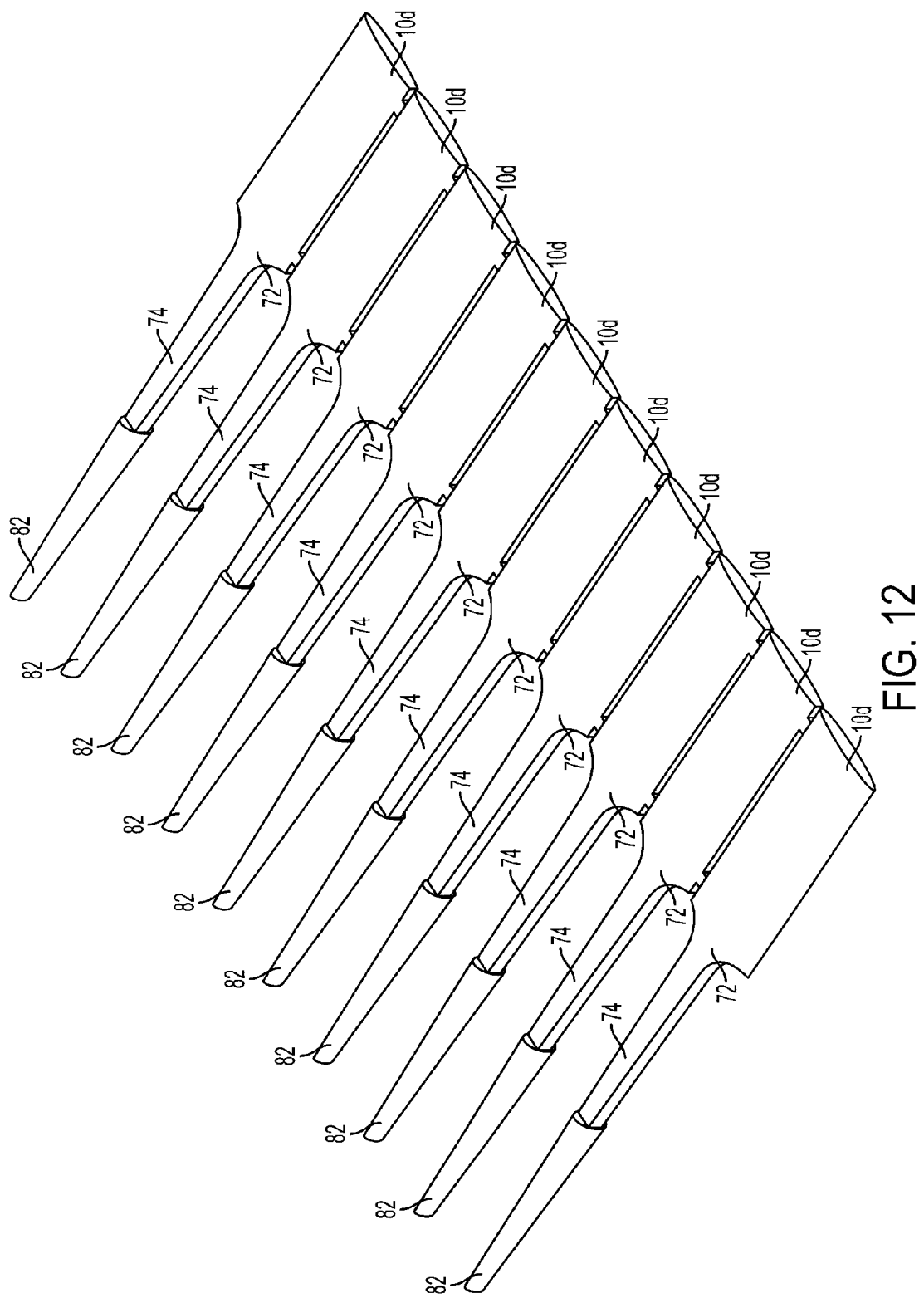
FIG. 12 is an isometric view of a fourth embodiment of interdental cleaners formed from the interdental cleaner blanks of FIG. 11, and including substantially frusto-conical cleaning heads.
Figure 13:
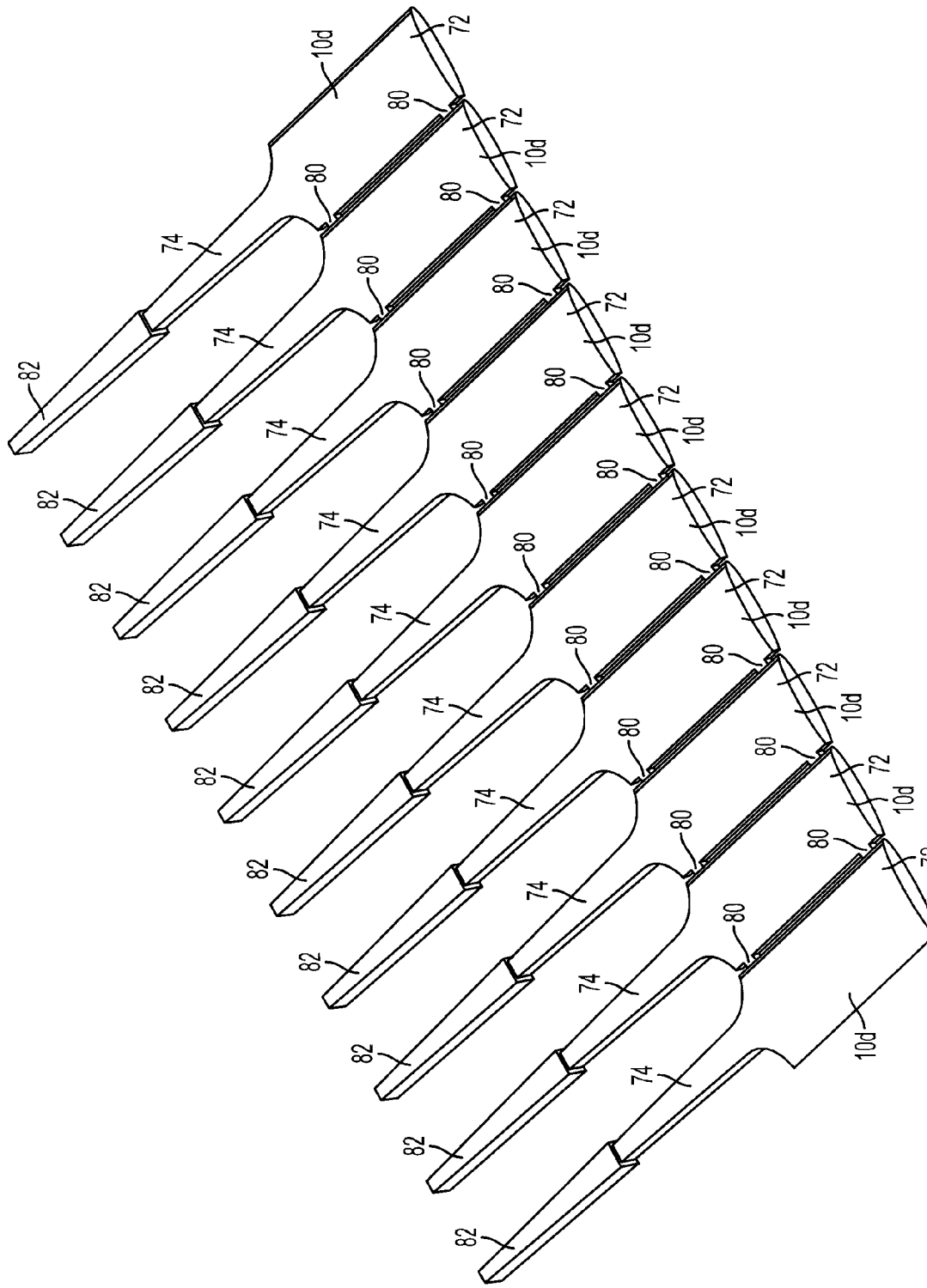
FIG. 13 is an isometric view of a fifth embodiment of interdental cleaners formed from the interdental cleaner blanks of FIG. 11, and including substantially rectangular cleaning heads.

FIGS. 10-13 illustrate a second embodiment of an extrusion (FIG. 10) that is formed into a fourth embodiment of an interdental cleaner 10d (FIGS. 12 and 13). FIG. 10 illustrates an extruded slug 60 of extrudable material that may include, for example, polypropylene (including glass-filled polypropylene) and/or nylon. The slug 60 is extruded in the direction of the arrow N to produce a midplane P and includes a plurality of sections 64 that extend across the width of the slug 60 and that include similar cross-sectional geometry. The cross-sectional geometry of each section 64 includes a relatively thicker central portion 66, and relatively reduced thickness end portions 68. Each section 64 is ultimately formed into an individual interdental cleaner 10d.

In the illustrated construction, the slug 60 includes a substantially constant cross section in the direction of extrusion N to simplify the extrusion process. As material is extruded, the slugs 60 are cut to length in increments that substantially correspond to the length of the finished interdental cleaner, although additional material may be included to facilitate handling during trimming and/or other manufacturing processes not necessarily explained herein.

FIG. 11 illustrates the slug 60 after a stamping process. After being extruded and/or cut to length, the slug 60 undergoes a stamping process which removes material from the slug 60 to form each section 64 into an individual cleaner blank 70. Each cleaner blank 70 includes a handle portion 72 and a shaft portion 74. Formation of the shaft portion 74 may include forming a tapered portion that reduces in cross section as it extends away from the handle portion 72. Formation of the handle portions 72 may include the addition of grips and/or the tapering of certain edges so as to better suit the grasping process and/or enhance aesthetic appeal. Other possible alterations to the handle portions 72 may include the addition of a company logo 76.

In the illustrated construction, the stamping process also removes material from between adjacent handle portions 72 to define a separation slot 78 and a plurality of connecting tabs 80. The slot 78 and the tabs 80 are configured to allow a plurality of interdental cleaners 10c to be packaged and handled as a single, continuous strip, while providing for the relatively quick and simple separation of individual interdental cleaners 10d by breaking of the tabs 80. The slots 78 and tabs 80 are configured so that this can be accomplished without damaging the individual cleaners 10d and with the use of a cutting device. For example, the tabs 80 are formed in the reduced-thickness end portions 68 of the slug sections 64.

FIGS. 12 and 13 illustrate strips of completed interdental brushes 10d. After the above-described extrusion and stamping processes, cleaning members 82 are formed on or coupled to at least the distal ends of the shaft portions 74 using cleaning member materials and overmolding or adhesion operations similar to those described above with respect to the cleaning members 10a, and 10b. The cleaning members 82 are generally formed of a material that is softer than the material that forms the cleaner blanks. For example, the cleaning members may be formed of a thermoplastic elastomer. The cleaning members 82 may be substantially conical in shape (FIG. 12), substantially rectangular (FIG. 13), or substantially any other cross-sectional shape. Although not specifically illustrated, the cleaning members 82 may also include various arrangements of bristles, such as those discussed above with respect to the cleaning members 10a, and 10b. Similarly, the cleaning members 82 (and bristles, if any) may include a textured surface that may or may not incorporate abrasives (e.g. pumice) to provide additional debris removal capability for the cleaning members 82. It should also be appreciated that other or additional manufacturing processes may also be employed to prepare the respective interdental cleaners 10c for commercial use. Possible flash and/or other remnants of the manufacturing process may be removed by tumbling, chemical cleaning, buffing, or other processes.

Figure 14:
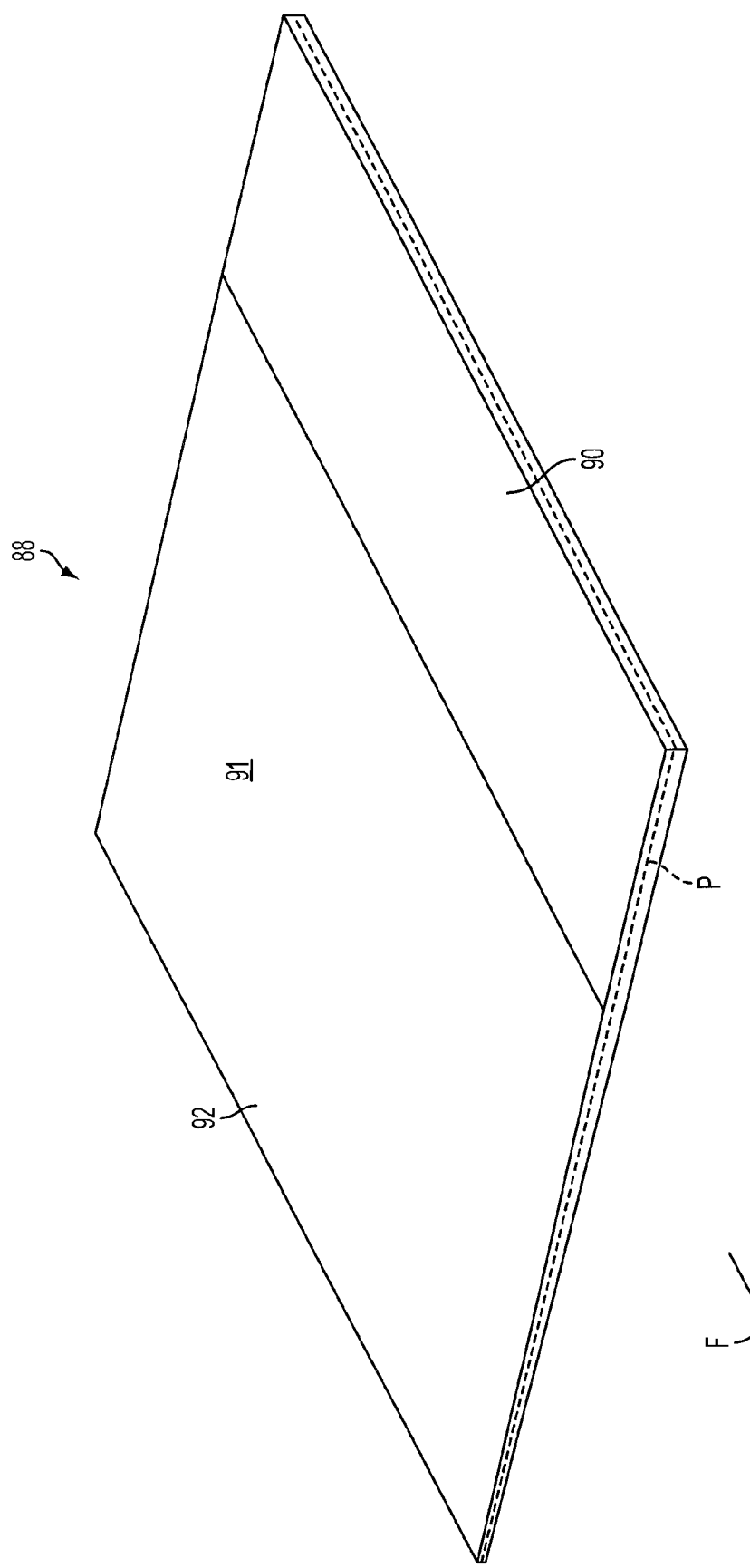
FIG. 14 is an isometric view of a third embodiment of extruded material from which interdental cleaner blanks are stamped.
Figure 15:
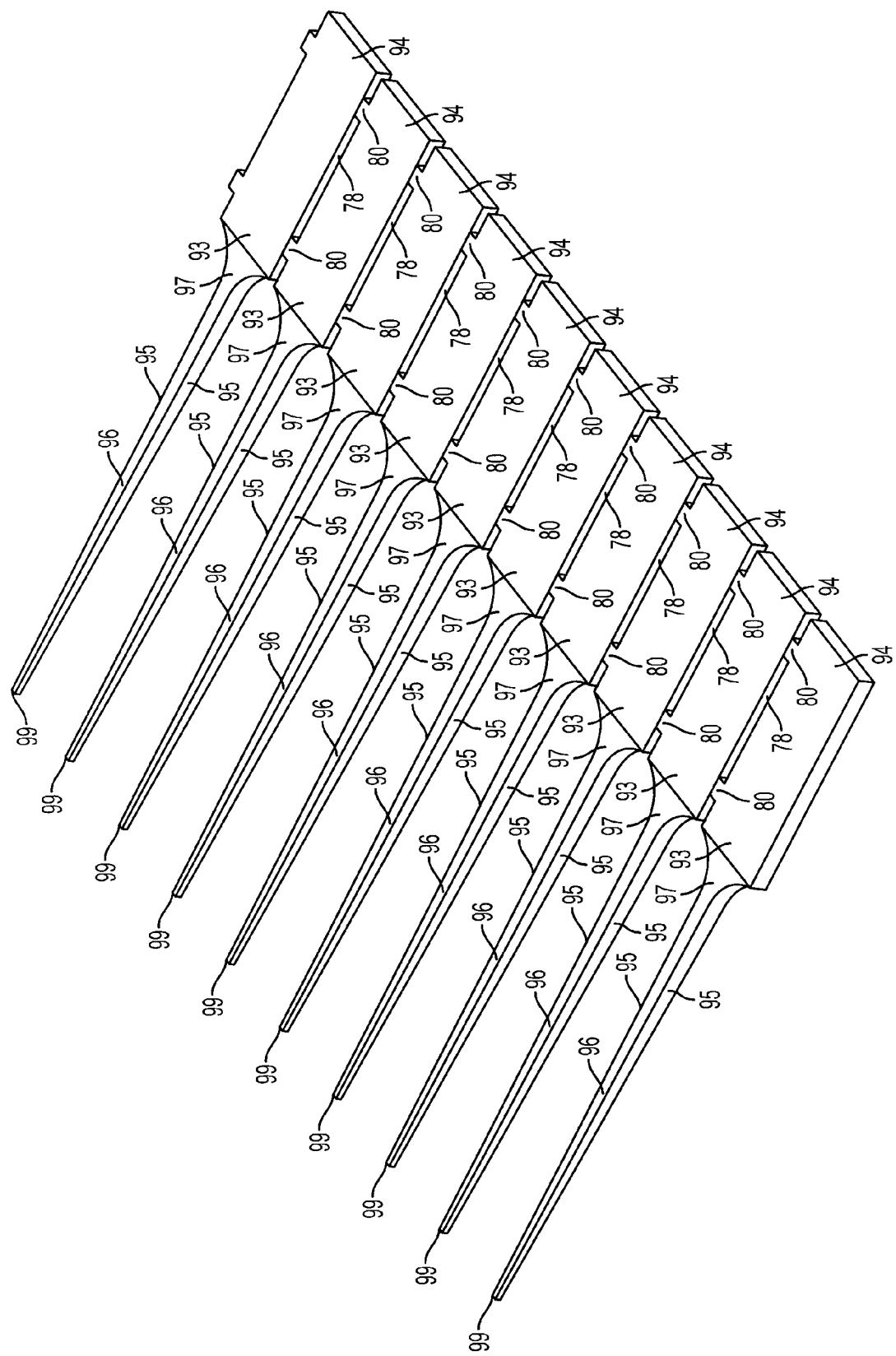
FIG. 15 is an isometric view of interdental cleaner blanks stamped from the extruded material of FIG. 14.
Figure 16:
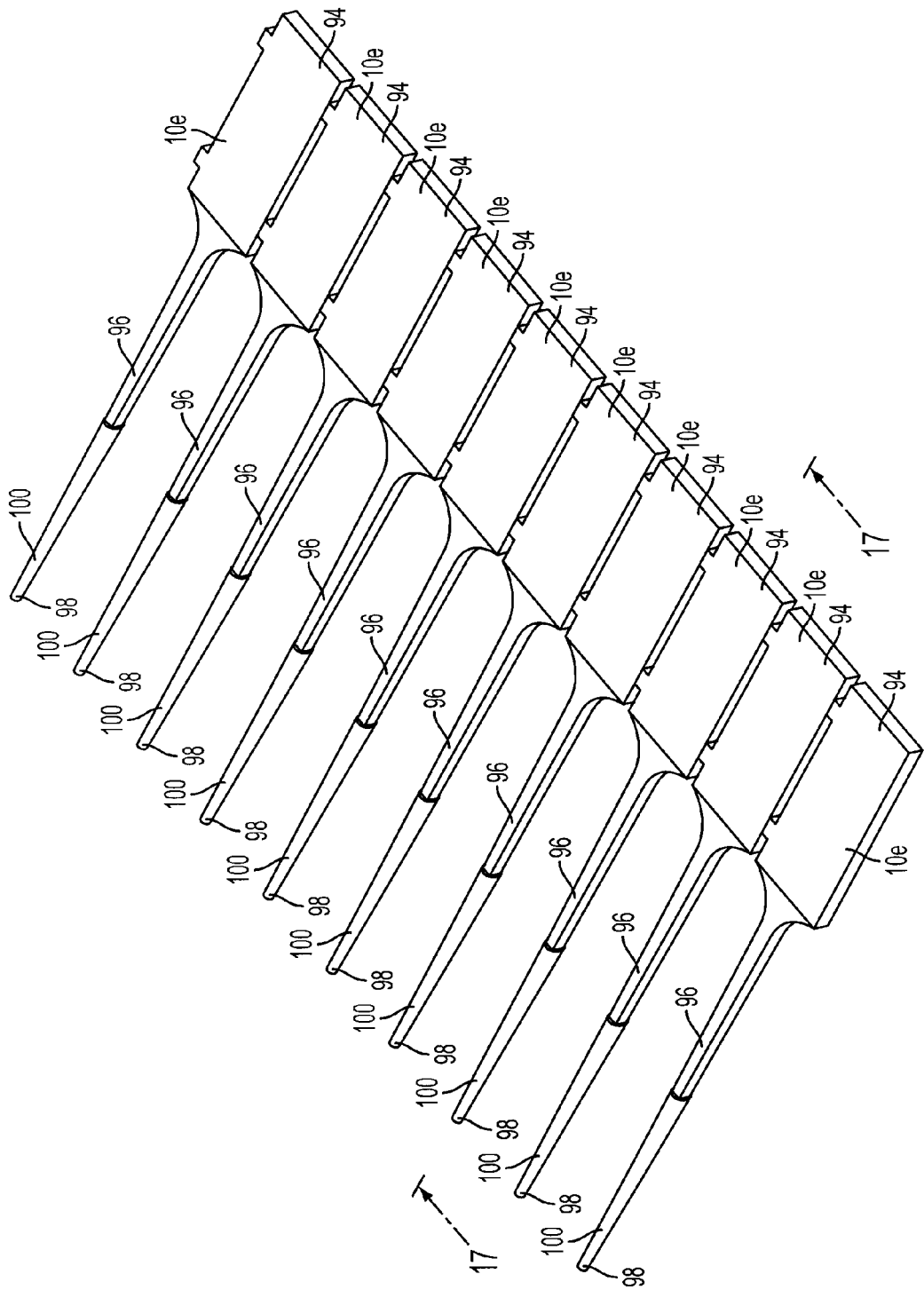
FIG. 16 is an isometric view of a sixth embodiment of interdental cleaners formed from the interdental cleaner blanks of FIG. 14.
Figure 17:
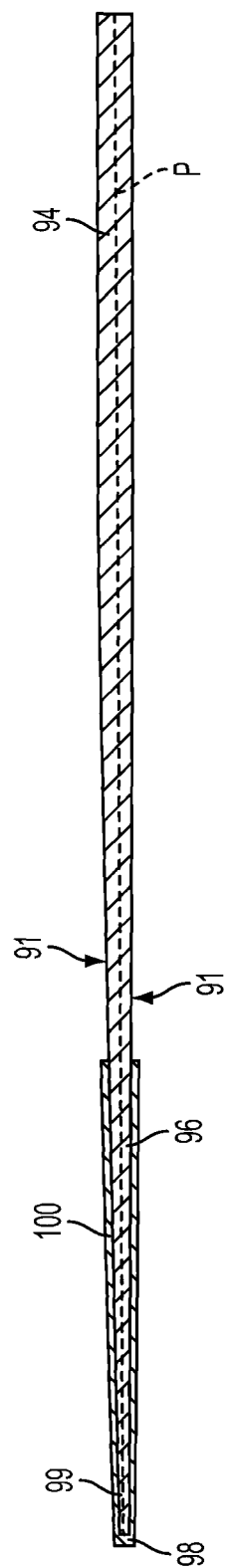
FIG. 17 is a cross-sectional view of one of the interdental cleaners of FIG. 16 taken along line 8-8.

FIGS. 14-17 illustrate a third embodiment of an extrusion (FIG. 14) that is formed into a fifth embodiment of an interdental cleaner 10e (FIGS. 16 and 17). FIG. 14 illustrates an extruded slug 88 that is extruded in a direction of extrusion F to define a midplane P. Whereas the slug 60 of FIG. 10 is extruded in a direction that is substantially parallel with the shaft portions 74 of the resultant interdental cleaners 10d, the slug 88 is extruded in the direction F that is substantially perpendicular to the shaft portions 74 of the resultant interdental cleaners 10e, for reasons discussed further below. The slug 88 includes a first portion 90 having a substantially uniform, e.g., rectangular, constant cross section, and a second portion 92 having a cross section that tapers toward a distal end of the second portion 92 that is opposite the first portion 90. The second portion 92 also defines a first pair of converging surfaces 91 (only one of the surfaces 91 is shown in FIG. 14) that face away from one another and converge toward the midplane P. Although each of the illustrated first pair of converging surfaces 91 is substantially planar, one or both of the converging surfaces may also be curved along all or a portion of its length.

As shown in FIG. 15, the slug 88 is subjected to a stamping process similar to that of the slug 60, to thereby form cleaner blanks 93 that each include a handle portion 94 formed from the first portion 90, and a shaft portion 96 formed from the second portion 92. The stamping process employed for the slug 88 may be similar to that discussed above with respect to the slug 60, and may similarly provide slots 78 and tabs 80 that allow individual interdental cleaners 10e to be snapped off of a continuous strip of interdental cleaners 10e without otherwise damaging the interdental cleaners 10e and without the use of a cutting device. As illustrated, the shaft portion 96 of each cleaner blank 93 tapers from a wide end 97 adjacent the first portion 90 to a narrow, distal end 99 opposite the wide end 97. The taper of each shaft portion 96 is defined by a second pair of converging surfaces 95 that face away from one another and that, like the converging surfaces 96, converge toward one another from the wide end 97 to the narrow distal end 99. Although a majority of each of the illustrated second pair of converging surfaces 95 is substantially planar, one or both of the converging surfaces 95 may also be curved along all or a portion of its length.

As illustrated in FIG. 16, after the cleaner blanks 93 have been formed by the extruding and stamping operations, cleaning members 100 are formed on or coupled to the shaft portions 96, generally on or adjacent to the distal ends 99, using cleaning member materials and overmolding or adhesion operations similar to those described above, thereby forming interdental cleaners 10e. It should also be appreciated that each of the manufacturing methods, materials characteristics, shapes, and bristle configurations of the various cleaning members discussed above may also be utilized for the cleaning members 100 of the interdental cleaners 10e.

In the embodiment of FIGS. 14-17, because the shaft portions 96 are not parallel with either the direction of extrusion or the direction of stamping, the shaft portions 96 may be formed with two pairs of converging surfaces (e.g., the first pair of converging surfaces 91 formed by extrusion, and the second pair of converging surfaces formed by stamping). This allows the distal end 99 of the cleaner blank 93, and thus the distal end 98 of the resulting interdental cleaner 10e (FIG. 16) to include a more sharply-defined pointed end relative to the distal ends of the interdental cleaners 10c or 10d, which generally taper in a single direction (e.g., the direction of stamping).

The invention claimed is:

1. A method for manufacturing interdental cleaners, the method comprising:

forming a slug by extruding material in a direction of extrusion, including forming a first slug portion including a first cross-section and a second slug portion including a second cross section different from the first cross-section, the extruded slug defining a midplane substantially parallel to the direction of extrusion;

stamping the slug in a direction of stamping that is substantially normal to the direction of extrusion thereby removing material to produce a plurality of cleaner blanks, each cleaner blank including a handle portion and a shaft portion, and oriented along the midplane such that the shaft portions extend substantially perpendicular to the direction of extrusion; and attaching a cleaning member to each shaft portion; wherein the stamping removes material from between adjacent handle portions to define a separation slot and a plurality of connecting tabs.

2. The method of claim 1, wherein forming the first slug portion includes forming the first slug portion such that the first cross-section is substantially rectangular.

3. The method of claim 1, wherein forming the second slug portion includes forming the second slug portion such that the second cross-section includes a first end adjacent the first slug portion and a second end opposite the first end, and wherein the second cross-section tapers from the first end to the second end.

4. The method of claim 1, wherein forming the slug further includes forming the slug out of at least one of polypropylene and nylon.

5. The method of claim 1, wherein forming the slug includes forming a slug of a first material, and attaching the cleaning member includes attaching a cleaning member formed of a second material that is softer than the first material.

6. The method of claim 1, wherein attaching the cleaning member further includes overmolding thermoplastic elastomer cleaning members over at least a portion of each shaft portion.

7. A method of manufacturing interdental cleaners, the method comprising:
forming a slug by extruding material in a direction of extrusion, including forming a first slug portion including a first cross-section and a second slug portion including a second-cross section different from the first cross-section, the slug defining a midplane and the second slug portion defining a first pair of converging surfaces that converge toward the midplane;
stamping the slug substantially normal to the direction of extrusion thereby removing material to form a plurality of cleaner blanks, each cleaner blank including a handle portion formed from the first slug portion and a shaft portion formed from the second slug portion, stamping the slug including forming each shaft portion to include a second pair of converging surfaces; and
attaching cleaning members to a portion of the shaft portion; wherein the stamping removes material from between adjacent handle portions to define a separation slot and a plurality of connecting tabs.

8. The method of claim 7, wherein stamping the slug to form a plurality of cleaner blanks further includes forming the shaft portions to extend substantially perpendicular to the direction of extrusion.

9. The method of claim 7, wherein forming the first slug portion includes forming the first slug portion such that the first cross-section is substantially rectangular.

10. The method of claim 7, wherein the second cross-section includes a first end adjacent the first slug portion and a second end opposite the first end, and wherein the second cross-section is at least partially defined by the first pair of converging surfaces and tapers from the first end to the second end.

11. The method of claim 7, wherein extruding the slug includes extruding the slug out of at least one of polypropylene and nylon.

12. The method of claim 7, wherein forming the slug includes forming a slug of a first material, and attaching cleaning members includes attaching cleaning members formed of a second material that is softer than the first material.

13. The method of claim 7, wherein attaching cleaning members includes overmolding thermoplastic elastomer cleaning members over at least a portion of the shaft portion.

14. A method of making interdental cleaners, the method comprising:
forming a slug by extruding material in a direction of extrusion to form a first slug portion having a first cross-section and a second slug portion adjacent the first slug portion and having a second cross-section different from the first cross-section;
stamping the slug substantially perpendicular to the direction of extrusion thereby removing material to form a plurality of cleaner blanks, including stamping the first slug portion to form handle portions of the cleaner blanks and stamping the second slug portion to form shaft portions of the cleaner blanks; and
attaching cleaning members to the shaft portions; wherein the stamping removes material from between adjacent handle portions to define a separation slot and a plurality of connecting tabs.

15. The method of claim 14, wherein forming the slug includes forming a slug of a first material, and attaching cleaning members includes attaching cleaning members formed of a second material that is softer than the first material.

16. The method of claim 14, wherein the first cross-section is substantially rectangular.

17. The method of claim 14, wherein the second slug portion includes a first end adjacent the first slug portion and a second end opposite the first end, and wherein the second slug portion defines a first pair of converging surfaces that converge towards the second end.

18. The method of claim 17, wherein each of the shaft portions include the first pair of converging surfaces and wherein stamping the slug forms at least one additional pair of converging surfaces that converge toward the second end.

19. The method of claim 14, wherein extruding the slug includes extruding the slug out of at least one of polypropylene and nylon.

20. The method of claim 14, wherein attaching cleaning members includes overmolding thermoplastic elastomer cleaning members over at least a portion of the shaft portions.

* * * * *